US010877029B2

(12) United States Patent
Fleming et al.

(10) Patent No.: US 10,877,029 B2
(45) Date of Patent: Dec. 29, 2020

(54) METHOD FOR THE PRODUCTION OF POLY(METHYL METHACRYLATE) (PMMA) MEMBRANES AND USES THEREOF

(71) Applicants: The Provost, Fellows, Scholars and other Members of Board of Trinity College Dublin, Dublin (IE); University College Cork—National University of Ireland, Cork, Cork (IE)

(72) Inventors: Peter Fleming, Cork (IE); Michael Morris, Dublin (IE); Thomas Fitzgerald, Kerry (IE); Ramesh Babu Padamati, Dublin (IE); Paul Delaney, Cork (IE); Clifton Ngan, Chelmsford, MA (US); Niamh Hennessy, Carrigtwohill (IE); Kamran Beyzavi, Carrigtwohill (IE)

(73) Assignees: The Provost, Fellows, Scholars and Other Members of Board of Trinity College Dublin, Dublin (IE); University College Cork—National University of Ireland, Cork, Cork (IE)

( * ) Notice: Subject to any disclaimer, the term of this patent is extended or adjusted under 35 U.S.C. 154(b) by 236 days.

(21) Appl. No.: 15/765,846

(22) PCT Filed: Oct. 7, 2016

(86) PCT No.: PCT/EP2016/074080
§ 371 (c)(1),
(2) Date: Apr. 4, 2018

(87) PCT Pub. No.: WO2017/060476
PCT Pub. Date: Apr. 13, 2017

(65) Prior Publication Data
US 2018/0284107 A1    Oct. 4, 2018

Related U.S. Application Data

(60) Provisional application No. 62/312,994, filed on Mar. 24, 2016.

(30) Foreign Application Priority Data

Oct. 8, 2015    (EP) .................................... 15189038

(51) Int. Cl.
*B01D 67/00*    (2006.01)
*G01N 33/50*    (2006.01)
(Continued)

(52) U.S. Cl.
CPC ....... *G01N 33/545* (2013.01); *B01D 67/0011* (2013.01); *B01D 67/0013* (2013.01);
(Continued)

(58) Field of Classification Search
CPC ............ B01D 67/0011; B01D 67/0013; B01D 67/0016; B01D 67/0018
See application file for complete search history.

(56) References Cited

U.S. PATENT DOCUMENTS 4,968,733 A    11/1990    Müller et al.
6,394,952 B1 *    5/2002    Anderson ............ G01N 21/474
                                                       600/300
(Continued)

FOREIGN PATENT DOCUMENTS

WO    WO-02/068517 A1    9/2002

OTHER PUBLICATIONS

Sakai et al. Poly(methylmethacrylate) membranes. Journal of Applied Polymer Science, vol. 22, No. 7, Jul. 1, 1978. pp. 1804-1815 (Year: 1978).*
(Continued)

*Primary Examiner* — Cachet I Proctor
(74) *Attorney, Agent, or Firm* — Cesari & McKenna, LLP

(57) ABSTRACT

A poly(methyl methacrylate) (PMMA) membrane having a highly porous, reticulated, 3-D structure suitable for lateral flow diagnostic applications is described. Also described is a method for producing a poly(methyl methacrylate) (PMMA) membrane that comprises the steps of mixing a suitable amount of PMMA, a solvent and a optionally one of either a co-solvent or a non-solvent to produce a solution, (Continued)

casting a thin film of the solution onto a support, and removal of the solvent from the solution to produce the PMMA membrane. A lateral flow diagnostic device comprising a highly porous PMMA membrane as a reaction membrane is also described.

16 Claims, 5 Drawing Sheets

(51) Int. Cl.
  *G01N 33/545* (2006.01)
  *B01D 69/02* (2006.01)
  *B01D 71/40* (2006.01)
  *G01N 33/543* (2006.01)
(52) U.S. Cl.
  CPC ..... *B01D 67/0016* (2013.01); *B01D 67/0018* (2013.01); *B01D 67/0088* (2013.01); *B01D 67/0093* (2013.01); *B01D 69/02* (2013.01); *B01D 71/40* (2013.01); *G01N 33/54366* (2013.01); *B01D 2323/02* (2013.01); *B01D 2325/02* (2013.01)

(56) References Cited

U.S. PATENT DOCUMENTS

| | | | | |
|---|---|---|---|---|
| 8,101,431 | B2* | 1/2012 | McDevitt | B01L 9/527 436/518 |
| 2002/0045195 | A1* | 4/2002 | Hubscher | G01N 33/558 435/7.9 |
| 2007/0296111 | A1* | 12/2007 | Reverchon | B01D 67/0016 264/172.16 |
| 2010/0028898 | A1* | 2/2010 | Aoki | G01N 21/6452 435/6.12 |
| 2011/0111122 | A1* | 5/2011 | Mues | B01D 67/0013 427/209 |
| 2014/0206103 | A1* | 7/2014 | Shin | G01N 21/7703 436/501 |
| 2016/0185087 | A1* | 6/2016 | Kian | B32B 27/18 264/400 |

OTHER PUBLICATIONS

Lai et al. On the Formation of macrovoids in PMMA membranes, Journal of Membrane Science, vol. 155, No. 1, Mar. 31, 1999 pp. 31-43 (Year: 1999).*
Silverstri et al. "Polymethyl methacrylate membranes with controlled porosity for advanced multi-step drug elution" Journal of Applied Biomaterials and Biomechanics. vol. 5, No. 2 May 1, 2007 pp. 95-106 (Year: 2007).*
Kosma et al. "Macrovoids in solution-cast membranes: Direct probing of systems exhibiting horizontal macrovoid growth", Journal of Membrane Science, Elsevier BV, NL, vol. 407, Mar. 10, 2012, pp. 93-107.
Lai et al. "On the formation of macrovoids in PMMA membranes", Journal of Membrane Science, Elsevier BV, NL, vol. 155, No. 1, Mar. 31, 1999.
Ruaan et al. "Factors affecting the nodule size of asymmetric PMMA membranes", Journal of Membrane Science, Elsevier BV, NL, vol. 190, No. 2, Sep. 15, 2001, pp. 135-145.
Sakai et al. "Poly(methyl Methacrylate) Membranes", Journal of Applied Polymer Science, vol. 22, No. 7, Jul. 1, 1978, pp. 1805-1815.
Silvestri et al. "Poly(methyl methacrylate) membranes with controlled porosity for advanced multi-step drug elution", Journal of Applied Biomaterials and Biomechanics, Wichtig Editore S.R.L., Milano, Italy, vol. 5, No. 2, May 1, 2007, pp. 95-106.

* cited by examiner

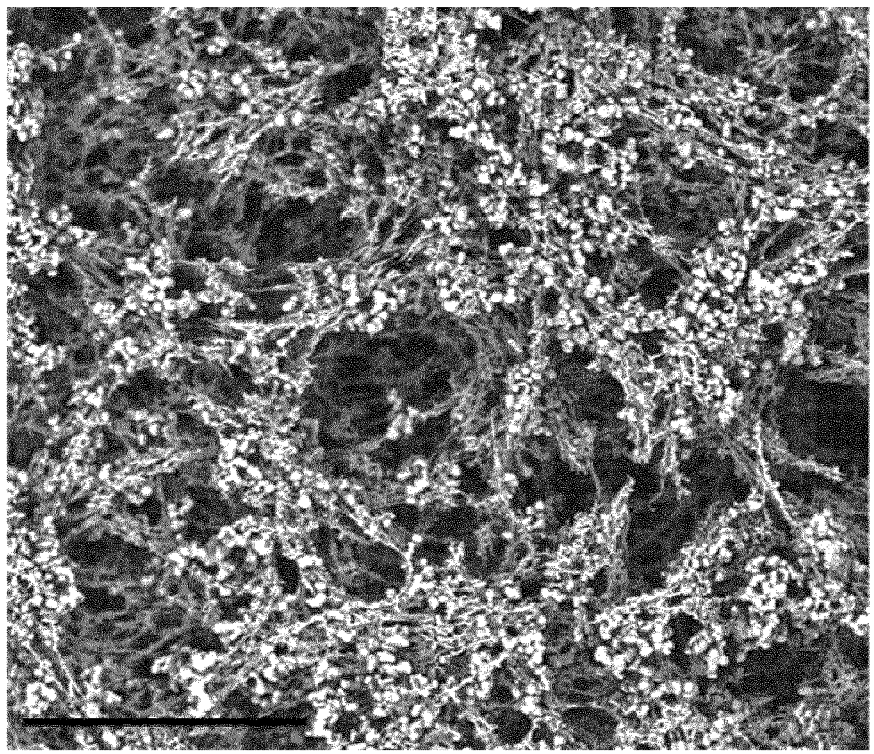
A
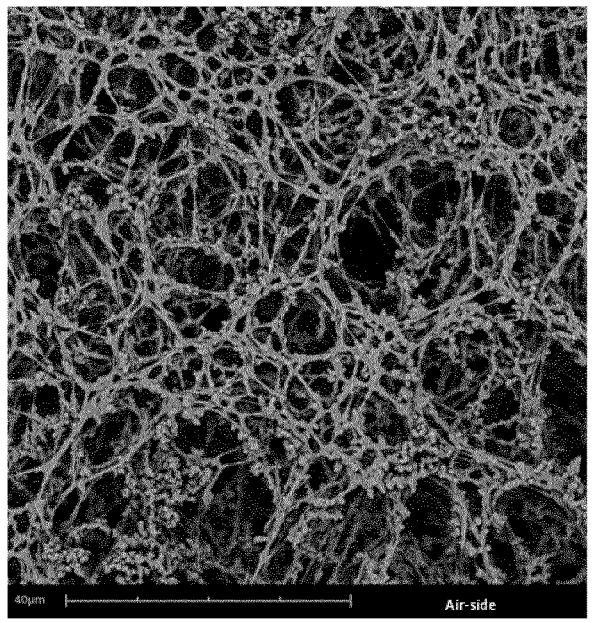
B
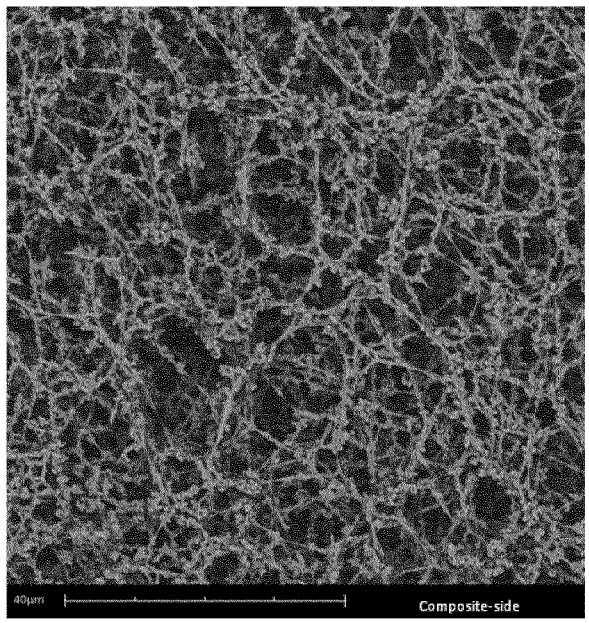
C
Figure 1

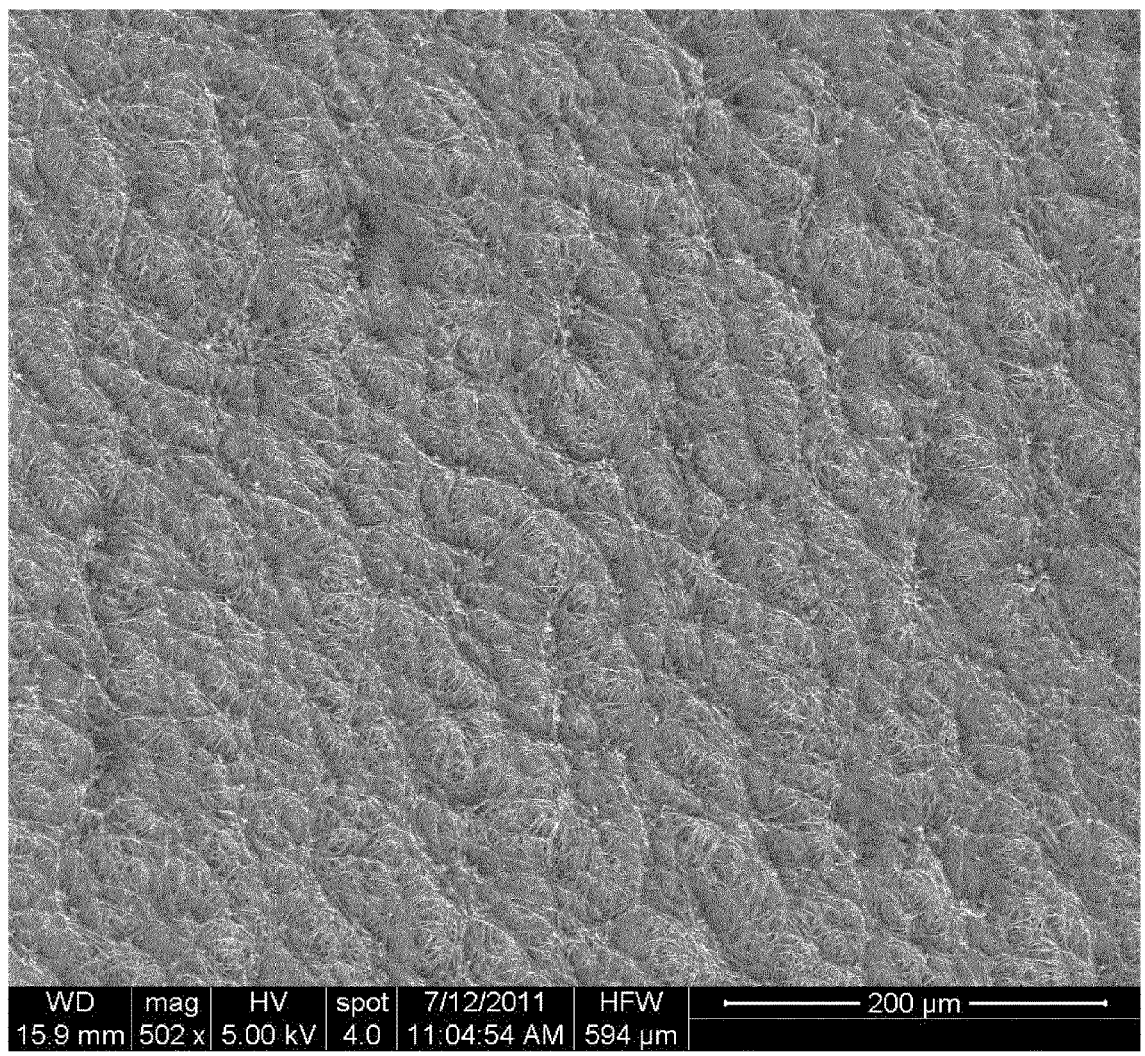
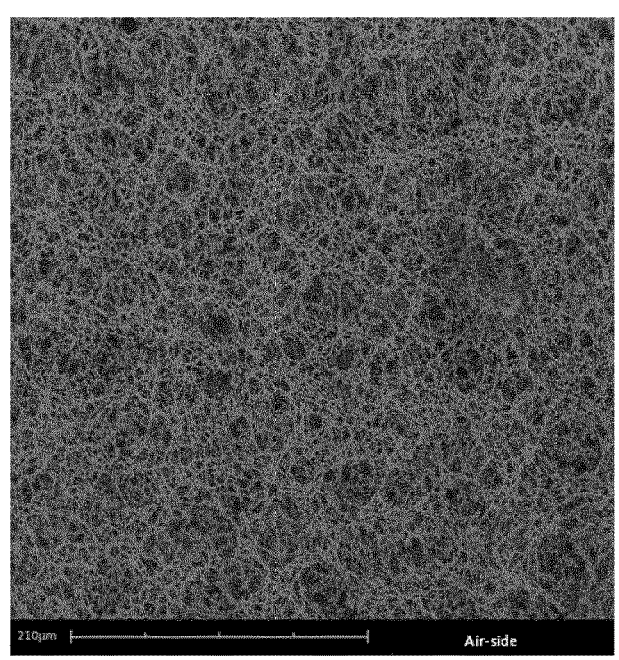
Figure 2A (above) and Figure 2B (below)

METHOD FOR THE PRODUCTION OF POLY(METHYL METHACRYLATE) (PMMA) MEMBRANES AND USES THEREOF

CROSS REFERENCE TO RELATED APPLICATIONS

This application is the National Stage of International Application No. PCT/EP2016/074080, filed on Oct. 7, 2016, which claims priority to European Application No. 15189038.1, filed on Oct. 8, 2015 and U.S. Application No. 62/312,994, filed on Mar. 24, 2016. The contents of each application are hereby incorporated by reference in their entirety.

FIELD OF THE INVENTION

This invention relates to poly(methyl methacrylate) (PMMA) membrane/support material composites and a method for producing the same. In particular, the invention relates to PMMA membranes, a method for the production of PMMA membranes, and the use of those membranes in lateral flow assays.

BACKGROUND TO THE INVENTION

Lateral flow diagnostics require a structure through which aqueous media incorporating detector particles (e.g., gold nanoparticles or latex beads) will pass through by means of capillary flow. This structure, typically a porous membrane, must possess sufficient pore size, porosity and uniformity to achieve suitable flow rates and allow even detector particle mobility while also having adequate protein binding capacity so that proteins will bind to the surface giving it assay functionality. The current membrane used in most commercial lateral flow diagnostics is a nitrocellulose membrane. Nitrocellulose has ideal protein binding properties for lateral flow diagnostics applications coupled with the ability to provide suitable and tunable pore size and porosity. Production of membrane from nitrocellulose is costly as the nitrocellulose raw material is inconsistent due to its production from natural sources (e.g. cotton linters and wood pulp). The formation of nitrocellulose membrane is carried out through a slow phase inversion process. Due to the nature of this process, it is very sensitive to the process environment and the properties of the raw materials including but not limited to polymer molecular weight and polydispersity. The slow phase inversion leads to slow production speeds and the sensitivity of the process results in the significant loss of out of specification product in quality control. These reliability issues make the production of nitrocellulose membrane problematic.

In addition, nitrocellulose is classified as a hazardous material, as it is highly flammable and will undergo auto-ignition when not stored under the correct conditions. These issues add to the cost of handling, shipping and storage, and its propensity to decompose over time results in a limited shelf-life of approximately 18 months to 3 years at which point the membrane becomes unusable and hazardous.

Silvestri et al. (Journal of Applied Biomaterials and Biomechanics, vol. 5(2), pp. 95-106 (2007)) describes the preparation of free-standing poly(methyl methacrylate) (PMMA) membranes on a glass substrate. Vassiliki et al. (Journal of Membrane Science, vol. 407, pp. 93-107 (2012)) describe solution-cast PMMA membranes. Lai J-Y, et al. (Journal of Membrane Science, vol. 155(1), pp. 31-43 (1999)) describes the preparation of free standing PMMA membrane adhered to a polyester support. However, the PMMA membranes described therein contain marcovoids which hamper later flow of fluids. Yoshitada et al. (Journal of Applied Polymer Science, vol. 22(7), pp. 1805-1815 (1978)) describes the preparation of free standing PMMA membrane that has film like properties rather than the high porosity and larger pore size associated with membrane systems for separation, filtration and other applications. U.S. Pat. No. 4,968,733 describes the preparation of both PMMA hollow fibres and free standing flat sheet PMMA membranes adhered to a polyester support.

There is therefore a need to provide a membrane for use in lateral flow diagnostics which overcomes at least one of the above-referenced problems.

SUMMARY OF THE INVENTION

The production of structures for use in lateral flow diagnostics may be problematic as it requires spatially homogeneous structures with large pore sizes, which are required to enhance capillary flow, reducing the time for the test to complete, and to allow for the uniform unhindered passage of large detector particles through the structure. All previous reported methods for the production of PMMA membranes result in low porosity with macrovoid formation and/or an asymmetric bicontinuous structure. High porosity is required to enhance the sensitivity of the assay by maximising the surface area available for protein binding applications. Currently, the market for lateral flow diagnostic membrane is dominated by nitrocellulose products.

Broadly, the invention is based on the discovery that PMMA membranes made using a thin film casting and solvent removal process, as described herein, can have a highly porous, symmetric reticulated, 3-D structure that enables capillary flow along the membrane. By forming the membrane on a suitable support material additional strength and durability can be imparted to the composite. When coupled with hydrophilisation techniques the resulting PMMA membrane has a protein binding capacity that is ideally suited for use in lateral flow diagnostic devices. Thus, the invention relates to methods of making the porous PMMA membrane/backing material composite, to applications of the membrane in lateral flow diagnostic devices, and to the porous PMMA membrane itself.

Thus, in one embodiment, there is provided, according to the appended claims, a method for producing a composite of a symmetric porous poly(methyl methacrylate) (PMMA) membrane and a solid support, the method comprising the steps of:
  (i) mixing a suitable amount of PMMA, a solvent and optionally a co-solvent and/or a non-solvent to produce a solution;
  (ii) casting a thin film of the solution onto a solid support material; and
  (iii) removal of the solvent from the cast solution to produce the PMMA membrane/solid support composite.

In another embodiment there is provided a method for producing a porous poly(methyl methacrylate) (PMMA) membrane, the method comprising the steps of:
  (i) mixing a suitable amount of PMMA, a solvent and optionally a co-solvent and/or a non-solvent to produce a solution;
  (ii) casting a thin film of the solution onto a support; and
  (iii) removal of the solvent from the cast solution to produce the PMMA membrane.

PMMA membranes produced according to the method of the invention have surprisingly been found to have a homogenous, highly porous and symmetric 3-D structure that is ideally suited to lateral flow diagnostic applications, for example, use as a reaction membrane in a lateral flow diagnostic device.

In some embodiments, the solid support material is selected from the group consisting of polyester, stainless steel, poly(methyl methacrylate), polystyrene, polypropylene or a combination thereof. In a particular embodiment, the support is polyester.

In some embodiments, the polymer solution is applied to the support material from a technique selected from the group consisting of a casting knife, a slot die coater, a dip coater or a roller coater. In a preferred embodiment, the solution application technique is a slot coater.

As used herein, the term "suitable amount" should be understood to mean an amount sufficient to produce a solution capable of being used to produce a porous membrane. In this specification, the term "porous" should be understood to mean a % porosity of at least 60% as determined by weight and volume calculations. Preferably, the % porosity should be at least 60%, 65%, 70%, 75%, 80%, 85%, 86%, 87%, 88%, 89%, 90%, 91%, 92%, 93%, 94%, 95%, 96%, 97%, 98% or 99%. Ideally, the % porosity should be at least 85%.

In a particular embodiment, the PMMA membrane is an evaporation-induced phase separation (VIPS)-cast porous PMMA membrane. In an alternative embodiment, the PMMA membrane is a liquid induced phase separation (LIPS)-cast porous PMMA membrane. In a further alternative embodiment, the PMMA membrane is hybrid-cast porous PMMA membrane. In another embodiment, the PMMA membrane is a temperature-induced phase separation (TIPS)-cast porous PMMA membrane. Ideally, the PMMA membrane is a combined temperature- and evaporation-induced phase separation (TVIPS)-cast porous PMMA membrane.

In one embodiment, the PMMA solution is heated to a temperature above an upper critical solution temperature of the solution in step (i), the PMMA membrane is then TIPS-cast in step (ii), wherein the PMMA solution is cooled by casting onto a surface below its upper critical solution temperature followed by removal of the solvent/non-solvent.

In one embodiment, the PMMA membrane is VIPS-cast in step (ii), wherein solvent and one or more co-solvents/non-solvents is removed from the cast solution in a sequential manner by evaporation that is controlled by air flow over the film.

In one embodiment, the PMMA membrane is LIPS-cast in step (ii), wherein the thin film of solution is immersed into a coagulation bath containing a non-solvent, and optionally a solvent, whereby exchange of solvent and non-solvent results in the formation of a symmetric porous membrane on a solid support material and avoids skin layer formation.

In one embodiment, the PMMA membrane is hybrid-cast in step (ii), in which solvent is removed from the solution by evaporation that is controlled by air flow over the membrane, whereby the membrane is then immersed into a coagulation bath containing a non-solvent whereby the final membrane structure is fixed.

In one embodiment, the PMMA membrane is temperature- and evaporation-cast, wherein the PMMA solution is heated to a temperature above an upper critical solution temperature of the solution in step (i). The PMMA membrane is then TVIPS-cast in step (ii), wherein the PMMA solution is cooled by casting onto a surface below its upper critical solution temperature; and solvent and one or more co-solvents/non-solvents are removed from the cast solution in a sequential manner by evaporation that is controlled by air flow over the film.

The term "TIPS-cast" as applied to PMMA membrane formation should be understood to mean that a membrane is produced by mixing PMMA with a solvent and optionally either one or more of a co-solvent or a non-solvent above the upper critical solution temperature (UCST) of the solution to produce a solution, the solution is then brought to within 5° C. above the UCST of the solution. This solution is then cast onto a flat support surface that is in the range of 2° C. to 12° C. below the USCT of the solution. The remaining solvents and/or co-solvents and/or non-solvents are removed by rapid evaporation or immersion in a water bath. Ideally, the cast solution is cooled to a temperature of 10° C. below its UCST. If the temperature is not controlled to within the specified range at each stage defects will occur including but not limited to skin layer formation, an asymmetric membrane structure and delamination of the membrane from the support material.

The term "VIPS-cast" as applied to PMMA membrane formation should be understood to mean that a membrane is produced by mixing PMMA with a solvent and optionally one or more of a co-solvent and/or a non-solvent to produce a solution, this solution is then cast onto a flat support surface whereby controlled evaporation of solvent and/or co-solvents and/or non-solvents in a sequential manner is controlled via a controlled air flow. As the solvent and/or co-solvents and/or non-solvents evaporate at different rates in a sequential manner (for example, from highest boiling point to lowest boiling point), the polymer precipitates forming the membrane and the extended evaporation process facilitates pore growth yielding a highly porous symmetric membrane.

The term "LIPS-cast" as applied to PMMA membrane formation should be understood to mean that the membrane is produced by mixing PMMA with a solvent to produce a solution. The solution is then cast onto a flat support surface and immediately immersed into a coagulation bath containing a non-solvent and optionally a solvent and/or co-solvent whereby exchange of solvent and non-solvent results in the formation of a porous membrane.

The term "hybrid-cast" as applied to PMMA membrane formation should be understood to mean that the membrane is produced by mixing PMMA with a solvent and optionally one or more of a non-solvent and/or co-solvent to produce a solution. The solution is then cast onto a flat surface in which evaporation of solvent is controlled for a defined period of time by air flow over the membrane. The membrane is then immersed into a coagulation bath containing a non-solvent and optionally a solvent and/or co-solvent whereby the final membrane structure is fixed.

The term "TVIPS-cast" as applied to PMMA membrane formation should be understood to mean that the membrane is produced by mixing PMMA with a solvent and optionally one or more of a co-solvent or a non-solvent above the upper critical solution temperature (UCST) of the solution to produce a solution, the solution is then brought to within 5° C. above the UCST of the solution. This solution is then cast onto a flat support surface that is in the range of 2° C. to 12° C. below the USCT of the solution. Ideally, the cast solution is cooled to a temperature of 10° C. below its UCST. If the temperature is not controlled to within the specified range at each stage defects will occur including but not limited to skin layer formation, an asymmetric membrane structure and delamination of the membrane from the support material. Prior to complete removal of solvent and/or co-solvents and/or non-solvents the cast film is passed into a chamber wherein the solvent and/or co-solvents and/or non-solvents are removed in a sequential manner via a controlled air flow. As the remaining solvent and/or co-solvents and/or non-solvents evaporate at different rates in a sequential manner (for example, from highest boiling point to lowest boiling point), the polymer precipitates forming the membrane and the extended evaporation process facilitates pore growth yielding a highly porous symmetric membrane.

In one embodiment, the support is cooled such that a temperature difference of 10° C. exists between the support temperature and the UCST of the solution.

In one embodiment, the solution comprises 2-14 wt % PMMA, 0-30 wt % non-solvent and 55-75 wt % solvent/co-solvent. In one embodiment, the solution comprises 5-15 wt % PMMA; 70-90 wt % solvent/co-solvent; and 0-25 wt % non-solvent. In another embodiment, the solution comprises 4-12 wt % PMMA; 72-82 wt % solvent/co-solvent; and 6-24 wt % non-solvent. In yet another embodiment, the solution comprises 7-10 wt % PMMA; 70-80 wt % solvent/co-solvent; and 10-20 wt % non-solvent. In a further embodiment, the solution comprises 7-10 wt % PMMA; 75-78 wt % solvent/co-solvent; and 12-17 wt % non-solvent. In a particular embodiment, the solution comprises 4-14 wt % PMMA; 55-96 wt % solvent/co-solvent; and 0-30 wt % non-solvent. In all scenarios, the total wt % of the PMMA, solvent and non-solvent together should not exceed 100%. The wt % of PMMA can be selected from 2, 2.2, 2.4, 2.6, 2.8, 3, 3.1, 3.2, 3.3, 3.4, 3.5, 3.6, 3.7, 3.8, 3.9, 4, 4.2, 4.4, 4.6, 4.8, 5, 5.2 etc. to 15 wt %, and all increments there between.

In some embodiments, the solvent is selected from the group consisting of dichloroethane, acetic acid, acetone, iso-propanol, n-propanol, n-butanol, chloroform, toluene, 1,4 dioxane, tetrahydrofuran, ethyl acetate, methyl ethyl ketone or a combination thereof. In a particular embodiment, the solvent is acetone. Acetone was found to act as a good solvent for PMMA and its volatility increases the cooling effect encountered during evaporation.

In some embodiments, the non-solvent is selected from the group consisting of methanol, ethanol, ethyl ether, water, glycerol, ethylene glycol, or a combination thereof. In some embodiments, the non-solvent is water or ethanol. In a particular embodiment, the non-solvent is ethanol. Aliphatic alcohols were found to act as good pore formers, as at elevated temperatures they act as co-solvents for PMMA but at lower temperatures they behave as non-solvents, thereby increasing the lacquer sensitivity to temperature fluctuations. Ethanol is a strong non-solvent in this system; however, ethanol aided in the speed of polymer dissolution during mixing and its volatility enhanced the cooling of the system while also decreasing the overall time required to complete the process.

In one embodiment, the solution further comprises a C2-C6 co-solvent. In a particular embodiment, the solution further comprises a C3-C6 co-solvent. In yet another embodiment, the co-solvent is a C2-C3 or a C3-C4 solvent. Ideally, the co-solvent is selected from the group comprising n-propanol, 2-propanol, 1-butanol, 2-butanol, tert-butanol, 2-Methylbutan-2-ol, 3-Methylbutan-2-ol, 2,2-Dimethylpropan-1-ol, Pentan-3-ol, Pentan-2-ol, Pentan-1-ol, 1-Hexanol, 2-Hexanol, 3-Hexanol, 2-Methyl-2-pentanol, 2,3-Dimethyl-2-butanol, 3-Methyl-3-pentanol, cyclo-hexanol. In a particular embodiment, the co-solvent is 1-butanol. 1-butanol acts as a weak non-solvent for PMMA at low temperatures and acts as a solvent at temperatures greater than 30° C. 1-butanol's low volatility and weak non-solvent interactions allowed for the formation of mechanically stable structures.

As used herein, the term "C2-C6 co-solvent" should be understood to mean an alcohol having between two and six carbon atoms and is selected from the group consisting of ethanol, n-propanol, iso-propanol, 1-butanol, 2-butanol, tert-butanol, 2-Methylbutan-2-ol, 3-Methylbutan-2-ol, 2,2-Dimethylpropan-1-ol, Pentan-3-ol, Pentan-2-ol, Pentan-1-ol, 1-Hexanol, 2-Hexanol, 3-Hexanol, 2-Methyl-2-pentanol, 2,3-Dimethyl-2-butanol, 3-Methyl-3-pentanol, cyclo-hexanol.

Ideally, the solution comprises 5 wt % PMMA; 40 wt % acetone; 27.5 wt % ethanol; and 27.5 wt % 1-butanol. Preferably, the solution comprises 3.7 wt % PMMA; 41.3 wt % acetone; 27.5 wt % ethanol; and 27.5 wt % 1-butanol.

In one embodiment of the invention, the PMMA membrane is further modified, by being rendered hydrophilic, by treatment with any one or more of the group comprising hydrolysis, aminolysis, silanisation, surfactants, ultraviolet radiation, plasma treatment, electron beam radiation and ozonation. In all cases, the modification is such that it renders the membrane hydrophilic, while maintaining the ability to bind proteins via hydrophobic interactions.

In one embodiment, the surfactant is selected from the group, including but not limited to, alkyl phosphates, alkyl phosphonates, alkyl sulphonates, sodium alkyl sulphates, sodium alkane sulphonates, sulpho carboxylates, sodium alcohol sulphates, alkyl amino acids or laureate carboxylic acids or a combination thereof.

As used herein, the term "upper critical solution temperature (UCST)" should be understood to mean the critical temperature above which a stable solution will exist and below which the solution becomes unstable resulting in precipitation of polymer from solution. This is measured by a method known to the person skilled in the art by simply withdrawing a 1 ml aliquot of the mixed solution into a glass vial. The vial is then sealed, placed in a jar of warm water and slowly cooled. The UCST is recorded as the temperature at which the vial becomes opaque.

As used herein, the term "dew point temperature" should be understood to mean the temperature at which the water vapour in a sample of air at constant barometric pressure condenses into liquid water at the same rate at which it evaporates. At temperatures below the dew point, water will leave the air. In the present invention, for example, if the dew point temperature is above 0° C. a porosity collapse and poor adhesion to the substrate is observed. The lower the dew point temperature the higher the observed porosity in the final structure.

As used herein, the term "support temperature" should be understood to mean the temperature of the support material unto which the PMMA solution is cast. If the support temperature is more than 10° C. below the UCST, structural defects are encountered, including but not limited to delamination, artefacts, longitudinal structural splitting. If the support temperature is above the UCST structural defects are encountered, including but not limited to delamination, skin layer formation and brittleness.

The embodiments described herein also relate to a porous symmetric PMMA membrane and solid support composite produced according to the methods described herein. Membranes produced by such methods can achieve a porosity of greater than 90%.

Further, embodiments described herein relate to the use of porous poly(methyl methacrylate) (PMMA) membrane as a reaction membrane in a lateral flow diagnostic device. The present invention is based, at least in part, on the discovery that PMMA membranes produced according to the methods described herein have a homogenous, highly porous, symmetric network with sufficient protein binding capacity that is suitable for use as a reaction membrane in lateral flow diagnostic devices. PMMA, being a synthetic polymer, is a more consistent polymeric raw material compared with naturally derived nitrocellulose. Therefore, a process for the production of PMMA membranes suitable for lateral flow diagnostics results in a more consistent membrane product. This process produces symmetric porous poly(methyl methacrylate) membranes/support material composites with sufficient pore structure and functionality so as to make them applicable in a range of applications. One particular application is use as a lateral flow diagnostic membrane in the healthcare industry. A new lateral flow membrane offers a good market opportunity to any membrane manufacturer.

The ability to produce appropriate membranes from a purely synthetic polymer (for example, PMMA) removes any issues associated with the use of raw materials derived from natural sources, thereby enabling the production of a more consistent product. This will reduce the loss of revenue during both production and when sold to customers, and also offers a more consistent product to customers.

In a further aspect, the invention relates to a porous PMMA membrane for use as a reaction membrane in a lateral flow diagnostic device.

Lateral flow diagnostic devices (also referred to as immunochromatographic strip tests) are well-known in the art and generally comprise a sample pad, a conjugate pad typically containing detection particles adsorbed with antibodies or antigens specific to the analyte being tested, a reaction membrane (also known as a solid-phase membrane or a capillary bed), and an absorbent pad.

Typically, the PMMA membrane has an analyte capture molecule immobilised to the membrane. The analyte capture molecule may be any molecule capable of binding to the analyte-target molecule complex, for example an antibody or antigen.

The embodiments described herein also relate to a PMMA membrane having a highly porous, symmetric reticulated, 3-D structure that is capable of allowing a liquid sample to move through the membrane by capillary action while simultaneously binding protein via hydrophobic interactions.

In one embodiment, there is provided a porous poly (methyl methacrylate) (PMMA) membrane/support material composite produced by the method described above.

In one embodiment, there is provided a porous poly (methyl methacrylate) (PMMA) membrane having a reticulated symmetric 3-D matrix structure and a porosity of at least 60%, as determined by weight volume calculations.

In one embodiment, there is provided a porous poly (methyl methacrylate) (PMMA) membrane having a reticulated symmetric 3-D matrix structure and a porosity of at least 85%, as determined by weight volume calculations.

In one embodiment, there is provided a porous poly (methyl methacrylate) (PMMA) membrane as claimed above having an average pore size of 0.5-30 µm.

In one embodiment, there is provided a use of a porous poly(methyl methacrylate) (PMMA) membrane described above for separation of one or more components from a fluid.

As used herein, the term "reticulated" should be understood to mean constructed, arranged, or marked like a net or network.

The embodiments described herein further relate to a highly porous and functional reaction membrane configured to allow a liquid sample (for example, spinal fluid, whole blood, serum, plasma, urine, culture media, aqueous buffer, saliva) and detector particles (for example gold, silver, paramagnetic, latex, carbon), to move through the membrane by capillary action, characterised in that the reaction membrane comprises a porous PMMA membrane.

Preferably, the PMMA membrane has a % porosity of at least 60% as determined by weight and volume calculations whereby:

$$\% \text{ porosity} = (1 - (\text{measured membrane density}/1.17)) \times 100$$

where,
    measured membrane density is calculated by dividing the weight of a piece of membrane, of known volume, by its volume (units of g/cm$^3$). In general, 1.17 g/cm$^3$ is taken as the density of non porous PMMA.

Typically, the porous PMMA membrane of this invention has an average pore size of 0.5 to 30 µm, the pore size can be measured routinely by bubble point. The bubble point of a membrane is the pressure required to force air through a wet membrane.

Thus, the embodiments described herein provide a PMMA membrane having a highly porous, reticulated symmetric, 3-D structure that is capable of allowing a liquid sample move through the membrane by capillary action, wherein the membrane has a % porosity of at least 60% and an average pore size of 0.5-30 µm. Ideally, the membrane has a % porosity of at least 85% and an average pore size of 0.5-30 µm.

In one embodiment, there is provided a lateral flow diagnostic device of the type comprising a reaction membrane, characterised in that the reaction membrane comprises a porous poly(methyl methacrylate) (PMMA) membrane as described herein and produced by the method as described herein.

In one embodiment, there is provided a device for performing an immunoassay that comprises a poly(methyl methacrylate) membrane. In a particular embodiment, the device is for use in a lateral flow immunoassay.

In one embodiment, the membrane has a sufficiently high binding capacity to retain capture zone molecules in lateral flow immunodiagnostic assay applications.

In one embodiment, the membrane has a fast and reproducible capillary flow rate.

In one embodiment, the membrane has a uniform capillary flow front when used in lateral flow applications.

BRIEF DESCRIPTION OF THE DRAWINGS

The invention will be more clearly understood from the following description of an embodiment thereof, given by way of example only, with reference to the accompanying drawings, in which:—

FIG. 1A is a scanning electron microscope (SEM) image of a typical PMMA membrane made by the methods described herein, illustrating the formation of highly porous networks through the membrane (Scale bar 50 µm), with FIG. 1B showing the air-side of the membrane, and FIG. 1C showing the composite-side of the membrane.

FIGS. 2A and 2B are top down SEM images of a typical PMMA membrane made by the methods described herein, illustrating the formation of highly porous networks through the membrane.

DETAILED DESCRIPTION OF THE INVENTION

Figure 3:
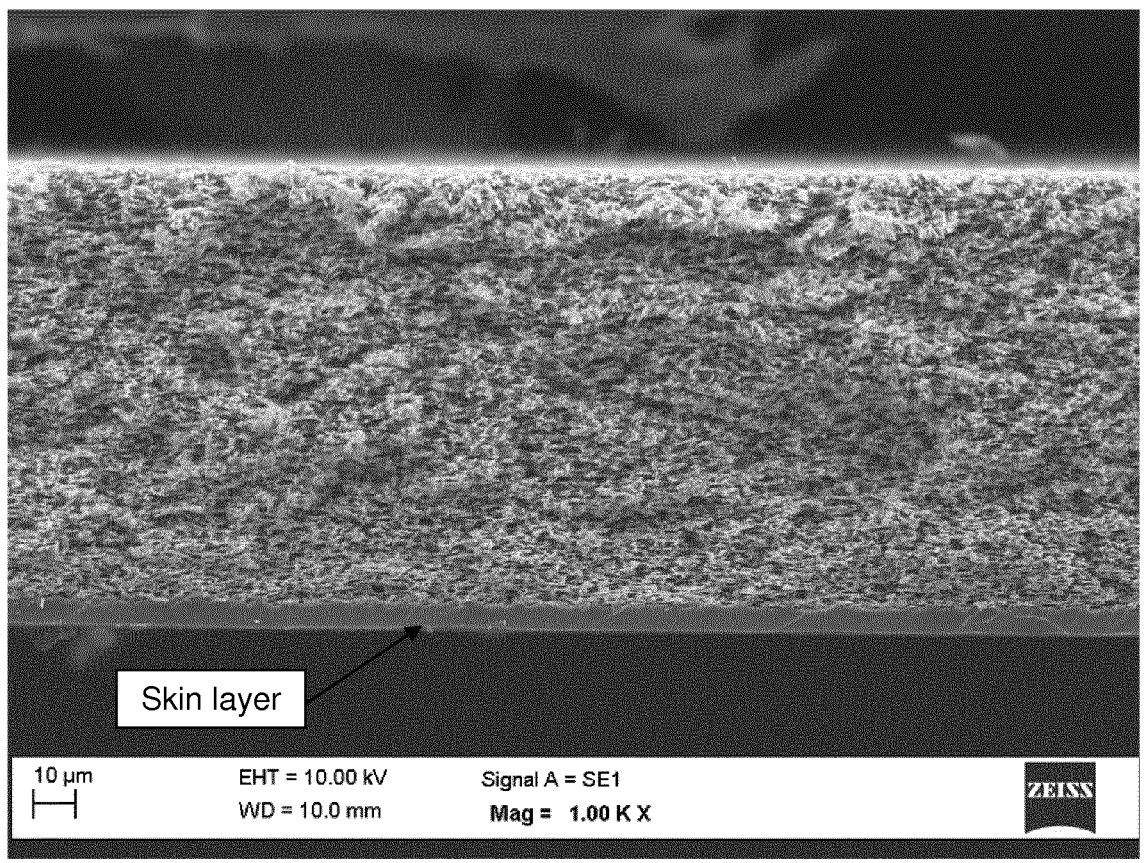
FIG. 3 is a cross-sectional SEM showing the formation of a bicontinuous PMMA membrane with a skin layer at the air interface and the underlying porous structure.

The most optimum membranes were formed from PMMA grades with a high molecular weight due to the increased viscosity of solutions with low polymer concentration. These low polymer concentration/high viscosity solutions resulted in more open structures formed upon phase inversion.

Solution production—Solutions for all experiments were produced as follows. The components were weighed into a glass jar and a magnetic stirring bar was placed into the jar. The jar was sealed and the solution was stirred on a magnetic stirring plate at speeds ranging from 50-400 rpm for three days at room temperature. Before casting, solutions were left to stand for 24 hours to degas.

VIPS-cast—Solutions were cast onto a polyester support using a k-control paint coater at a casting thickness of 250 μm. The cast solutions were left to form a membrane in ambient atmosphere. Once dried, the membranes were stored in a sealed dry environment.

Hybrid-cast—Membranes were VIPS-cast as described above. After a certain period of time of between 1 second and 15 minutes, the forming membrane was transferred into a coagulation bath consisting of either water, ethanol, methanol, acetone, toluene, 1,4,dioxane, tetrahydrofuran or a mixture thereof to complete the formation process. The coagulation bath was kept at a temperature of between 0° C. and 35° C. The formed membrane was then dried in ambient air and stored as before.

TIPS-cast—Solutions were formed into desired thin film shapes as described above. The films were then placed in contact with a cooling substrate with a temperature difference of between 0° C. and 10° C. below that of the upper critical solution temperature of the solution. The liquid components of the solutions were then removed through evaporation.

In some embodiments, PMMA membrane described herein is produced according to a 3 step process. Step one entails the production of a specialised solution (a mixture of polymer, solvent and non-solvent). Step 2 involves casting a thin film of this specialised solution onto a polyester support and passing this through a controlled atmosphere to induce formation and evaporate the solvent creating the polymeric membrane. Finally, step 3 involves the surface modification of the formed membrane towards lateral flow functionality.

The optimum range for the composition was found to have a PMMA concentration of 4-14 wt % and between 31-75 wt % solvent (typically acetone) (or 55-96 wt % solvent/co-solvent when used in combination); 20-65 wt % non-solvent/co-solvent combination (i.e. ethanol and 1-butanol) or 0-30 wt % non-solvent (i.e. water). In these systems, the acetone acts as a solvent for the PMMA while the aliphatic alcohols act initially as a co-solvent and then as a non-solvent. The membrane forms through a phase inversion process induced by a sudden drop in temperature via contact with a cooling substrate that is at a temperature below the UCST of the solution. Once phase inversion has occurred, the remaining solvent, co-solvents and non-solvents are removed by evaporation. This formation process results in the most open membranes being formed when the temperature difference between the cooling substrate and the UCST is large.

The addition of co-solvent(s) alone to the composition (from 20-65 wt %), while optional, result in a better control of the formation process. The co-solvent(s) in question are generally alcohols, typically C2-C6 alcohols, ideally selected from the group consisting of ethanol, n-propanol, iso-propanol, 1-butanol, 2-butanol, tert-butanol, 2-Methylbutan-2-ol, 3-Methylbutan-2-ol, 2,2-Dimethylpropan-1-ol, Pentan-3-ol, Pentan-2-ol, Pentan-1-ol, 1-Hexanol, 2-Hexanol, 3-Hexanol, 2-Methyl-2-pentanol, 2,3-Dimethyl-2-butanol, 3-Methyl-3-pentanol and cyclo-hexanol. Optimum results in this case, however, were found for C3 to C4 alcohols namely—n-propanol, 2-propanol, 1-butanol, 2-butanol and tert-butanol. The addition of these co-solvents boosts the solubility of PMMA in the resulting solutions and increases the solutions sensitivity to temperature fluctuations.

These solutions are cast onto a polyester support and passed under a casting knife set to a preferred height 250 μm, however, a height range of 50-400 μm was found to be effective. Upon passing under the casting knife the formed shape is cooled via contact with a cooling substrate. The solvent and non-solvents are then removed via evaporation or extraction in a non-solvent coagulation bath.

Highly porous reticulated networks are formed in a typical PMMA membrane produced by the method described herein, as illustrated in FIGS. 1 and 2. The % porosity of the membrane is greater than 60% as determined by weight and volume calculations, described previously.

Membrane surface modification to optimise functionality toward lateral flow diagnostics was carried out by a number of different methods, including treatment with aqueous solutions of surfactants, whereby the membrane is immersed in a surfactant solution for 1 minute, removed and dried in air.

In another approach, the membrane is exposed to ultraviolet radiation at wavelengths within the range of 100-400 nm for periods ranging from 30 minutes to 3 hours.

In yet another approach, the membrane is exposed to an oxygenated environment which is subsequently converted to ozone upon UV irradiation. Over a period of 30 minutes to 3 hours, the ozone produced oxidises the membrane surface rendering it more functional.

In still another approach, the membrane is treated with an acidic or a basic aqueous solution or a combination thereof to hydrolyse the surface. The membrane is treated in the acidic or basic solutions, at concentrations within the range of 0.1 M to 10 M, for periods of 1 hour to 24 hours with continuous agitation rendering the surface more hydrophilic.

Surface modification of the membrane was carried out on dried membrane by immersion in a surfactant bath followed by drying in air. The resulting membrane exhibited good functionality in promoting lateral flow of aqueous solutions through the membrane without deleteriously affecting the protein binding of the membrane.

The membrane produced by the method of the present invention can be used in lateral flow diagnostic assays. An example of such assays are medical diagnostics (HIV, hepatitis B, hepatitis C, flue etc), women's health (pregnancy & ovulation), blood banking (blood typing), animal health (heartworm, FIV, rabies, tuberculosis) and food safety (*Salmonella, E. coli, Listeria* etc.).

Bicontinuous Structural Formation

An example of a bicontinuous PMMA membrane produced by this method is given in FIG. 3. It was based, in part, on the discovery that a bicontinuous structure consisting of a dense skin layer at the air interface with an underlying porous structure could easily be produced by a simple alteration of the period of time between when the solution is formed into the desired shape and when it undergoes spinodal decomposition. Skin layers can be produced with a thickness in the range of 1 μm to 30 μm, through the thermodynamically induced precipitation of polymer at the air interface during evaporation of volatile solution components. The method follows the same process as described above with the inclusion of this slight delay in spinodal decomposition. The delay required was found to be greater than 10 seconds. The best method for achieving this delay was found to be altering the temperature difference between the solution UCST and the cooling platform temperature, so that the solution's UCST is in the order of 2 to 15° C. below the temperature of cooling platform. This allows for appropriate evaporation of solution components prior to spinodal decomposition. The structures formed, as illustrated in FIG. 3, are free of macrovoid defects that are commonly observed in PMMA bicontinuous membranes produced prior art methods.

Example 1

Fabrication of Porous PMMA Membrane

All solvents and non-solvents used were purchased from Sigma-Aldrich Ireland Ltd, Wicklow, Ireland. PMMA was purchased from Arkema Italy, Milan, Italy.

A typical PMMA membrane, as described herein, was formed as follows: A solution was formed of the following components: 5 wt % PMMA; 40 wt % acetone; 27.5 wt % ethanol; and 27.5 wt % 1-butanol. This solution is temperature sensitive whereby below a certain temperature, i.e., the upper critical solution temperature (UCST), the solution becomes unstable and separates out into two phases. Above the UCST, the solution is homogeneous and stable. In the process described herein, the UCST is used to induce the structural formation of the porous membrane. It is believed that the UCST is the point at which the aliphatic alcohol components, especially the 1-butanol, transition from being a co-solvent in the system to becoming a non-solvent (when transitioning through the UCST from higher to lower temperatures). In this example, the solution is formed into a desired shape and then cooled through contact with a substrate that is 0-10° C. below the UCST of the system. The remaining solvent and non-solvent is then removed via evaporation in a low humidity environment <30% RH at 25° C. This formation process results in the largest pore size membrane when using a large UCST—cooling substrate temperature difference, i.e. 10° C. Large temperature differences can, however, cause delamination from the support material and visual defects in the membrane. Using low temperature differences 0-3° C. result in more homogeneous structures with lower pore sizes.

Highly porous reticulated networks are formed in a typical PMMA membrane produced by the method described herein, as illustrated in FIGS. 1 and 2. The % porosity of the membrane is greater than 60% as determined by weight and volume calculations, described previously.

Membrane surface modification to optimise functionality toward lateral flow diagnostics was carried out by a number of different means including, treatment with aqueous solutions of surfactants, whereby the membrane is immersed in a surfactant solution for 1 minute, subsequently removed and dried in air.

Surface modification of the membrane was carried out on dried membrane by immersion in a surfactant bath followed by drying in air. The resulting membrane exhibited good functionality in promoting lateral flow of aqueous solutions through the membrane without deleteriously affecting the protein binding of the membrane.

There is provided, as described herein, a fast method for producing highly porous (>85%) structures with open air interfaces, as illustrated in FIG. 1. All previous reported methods for the production of PMMA membranes result in much lower porosity with macrovoid formation and/or a bicontinuous structure.

Figure 5:
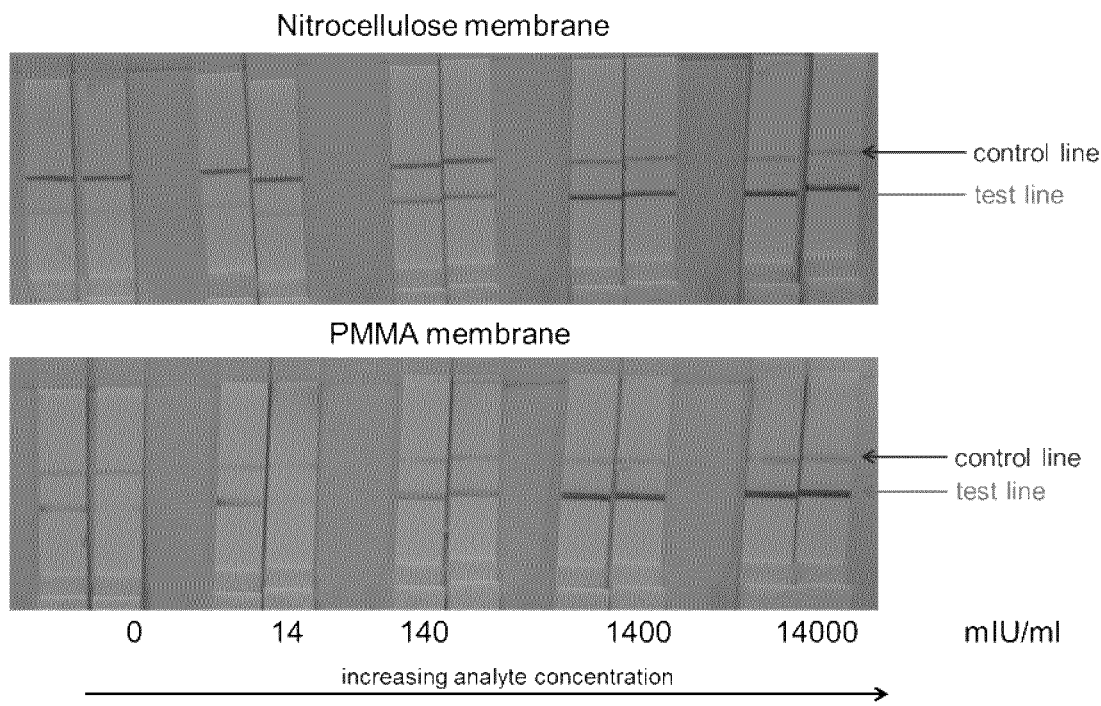
FIG. 5 is a photograph of a typical PMMA membrane produced by the methods described herein, illustrating the functionality of the membrane in a bioassay. Two common assays were tested, namely, the Human Chorionic Gonadotropin (hCG) and Hepatitis B Surface Antigen (HBsAg) assays. This photograph illustrates an hCG assay of various analyte concentration for both commercial nitrocellulose membrane and PMMA membrane described herein.
Figure 6:
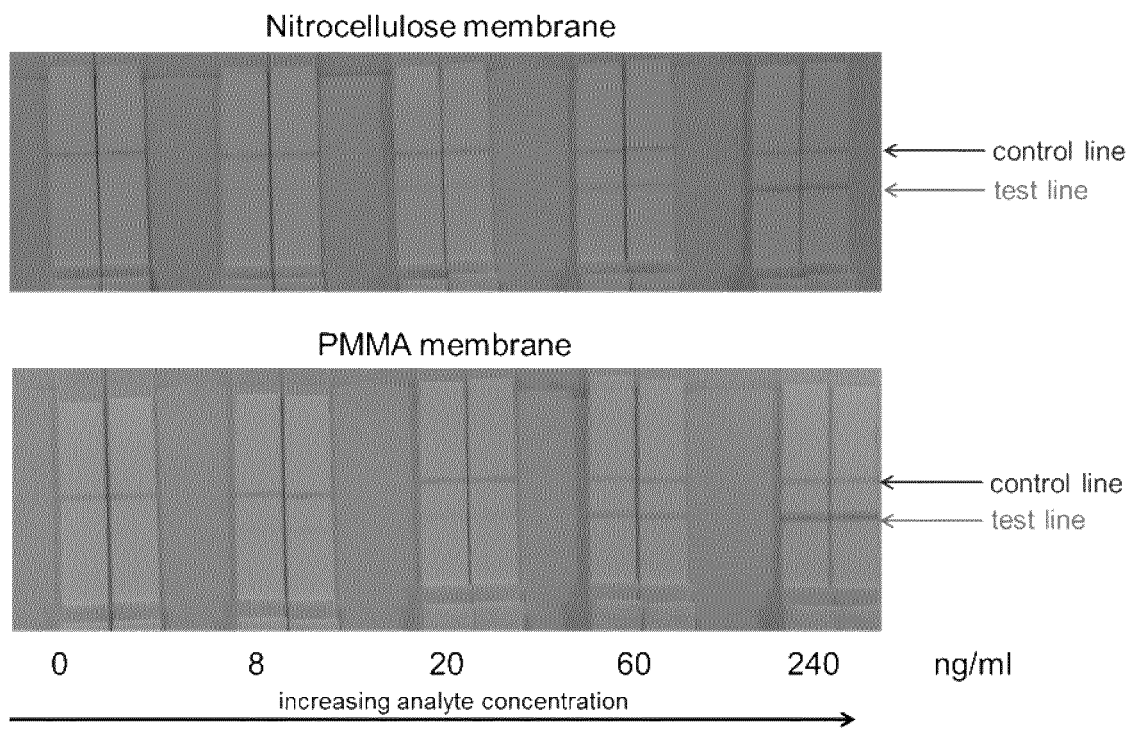
FIG. 6 is a photograph of a typical PMMA membrane produced by the methods described herein, illustrating the functionality of the membrane in a bioassay. Two common assays were evaluated, namely, the Human Chorionic Gonadotropin (hCG) and Hepatitis B Surface Antigen (HBsAg) assays. This photograph illustrates an HBsAg assay of various analyte concentrations for both commercial nitrocellulose membrane and PMMA membrane.

The PMMA structures described herein have shown excellent application results in lateral flow diagnostics (see FIGS. 5 and 6). The production of structures for use in lateral flow diagnostics is problematic as it requires spatially homogeneous structures with large pore sizes in the range of between 0.5 to 30 micrometers and a porosity of greater than 85%. Large pore sizes are required to enhance capillary flow, reducing the time for the test to complete, and to allow for the passage of large detector particles through the structure. High porosity is required to enhance the sensitivity of the assay.

The methods disclosed herein for the production of porous PMMA structures address some of problems in the industry, as outlined below;

- The fast formation process decreases the reliance of the process on the polymer raw material properties. This will allow for greater production speeds and a reduction in lost product from quality control.
- The polymer, PMMA, is a non-hazardous polymer which simplifies handling, shipping and storage considerations.
- PMMA does not show the same propensity towards decomposition as nitrocellulose, thus allowing for longer product shelf life.

Example 2

Use of Porous PMMA Membrane as Reaction Membrane in Lateral Flow Diagnostic Assay Membrane produced by VIPS-casting was assessed for application performance. Application performance was assessed under two categories—bead mobility and assay functionality. Bead mobility was assessed using 40 nm gold nano particles diluted in a solution of Phosphate Buffer Solution, Tween 20 and Bovine Serum Albumin.

Figure 4:
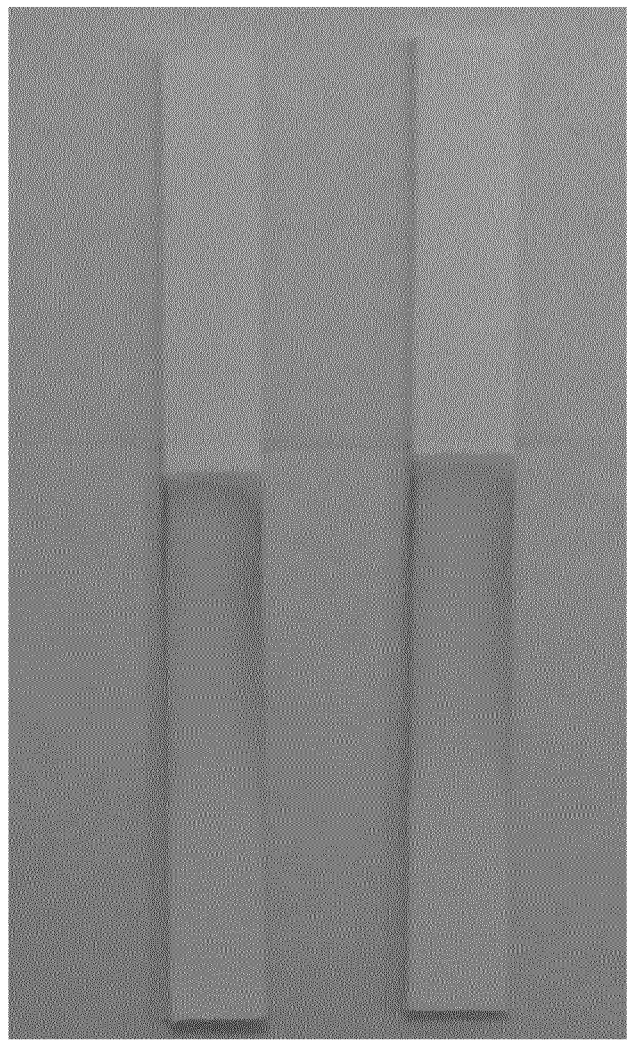
FIG. 4 is photograph of a typical PMMA membrane produced by the methods described herein, illustrating bead mobility. Bead mobility was assessed using 40 nm gold particles. The gold nanoparticles displayed mobility through the membrane.

Membrane samples 4.5 mm×25 mm were placed in 25 μL of bead solution and visually assessed for bead mobility. The gold nanoparticles showed good mobility through the membrane with no bead/liquid front separation (FIG. 4).

Functionality was assessed using a hepatitis B and pregnancy lateral flow test using membranes produced by TIPS-casting. PMMA membrane samples were spotted with a capture (against a target analyte) and control antibody and then fully dried to fix the antibodies in place. Membrane samples were then assembled with a conjugate pad (gold or latex detector particle conjugated with a detection antibody), sample pad (treated with buffer, surfactant and blocking solution) and absorbent pad. Membrane cards were cut into 5 mm wide test strips and run using 150 µL of positive (two signals) and negative (one signal) analyte (antigen in urine/serum/blood) solution. As the positive analyte solution passed through the conjugate pad, it re-mobilised the dried conjugate, and the antigen interacted with the conjugate (detector antibody/gold particle), both migrated through the porous network until they reached the capture and control zone. At the capture zone the antigen and conjugate were captured by the fixed antibodies and a red signal caused by the gold or latex detector particle was observed. With a negative solution the detector particle was not captured by the fixed antibody as there was no antigen present and the sandwich complex did not form (FIG. 5 and FIG. 6).

As used herein, the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiments described herein, but may be varied in both construction and detail.

The invention claimed is:

1. A method for producing a homogenous and symmetric poly(methyl methacrylate) (PMMA) membrane on a solid support material, the method comprising the steps of:
    (i) mixing a suitable amount of PMMA, a solvent, and a $C_2$-$C_6$ co-solvent to produce a PMMA solution with increased sensitivity to temperature fluctuations, wherein the $C_2$-$C_6$ co-solvent functions as a solvent above a certain temperature and as a non-solvent below said certain temperature;
    (ii) casting a thin film of the PMMA solution onto a solid support material; and
    (iii) affecting the temperature of the cast PMMA solution on the solid support material so that the cast PMMA solution becomes unstable and separates out into two phases, wherein the $C_2$-$C_6$ co-solvent transitions from a co-solvent in the solution to a non-solvent, thereby producing the homogenous and symmetric PMMA membrane on the solid support material.

2. The method according to claim 1, in which the PMMA solution is heated to a temperature above an upper critical solution temperature of the solution in step (i), the PMMA membrane is then TIPS-cast in step (ii), wherein the cast solution is cooled by casting onto a surface below its upper critical solution temperature followed by removal of the solvent/co-solvent.

3. The method according to claim 1, in which the PMMA membrane is VIPS-cast in step (ii), wherein solvent and co solvents is removed from the PMMA solution in a sequential manner by evaporation that is controlled by air flow over the PMMA solution.

4. The method according to claim 1, in which the PMMA membrane is LIPS-cast in step (ii) and the thin film of the PMMA solution is immersed into a coagulation bath containing a non-solvent and optionally a solvent, whereby exchange of solvent and non-solvent results in the formation of a symmetric porous PMMA membrane on a solid support material and avoids skin layer formation; wherein the non-solvent is selected from the group consisting of ethyl ether, water, glycerol, ethylene glycol, methanol and ethanol, or a combination thereof.

5. The method according to claim 1, in which the PMMA membrane is hybrid-cast in step (ii), the solvent and co-solvent are removed from the PMMA solution by evaporation that is controlled by air flow over the PMMA membrane, and the PMMA membrane is then immersed into a coagulation bath containing a non-solvent whereby the final PMMA membrane structure is fixed.

6. The method according to claim 1, in which the PMMA membrane is temperature- and evaporation-cast, wherein the PMMA solution is heated to a temperature above an upper critical solution temperature of the solution in step (i); the PMMA membrane is then TVIPS-cast in step (ii), wherein the PMMA solution is cooled by casting onto a surface below its upper critical solution temperature, and wherein solvent and co-solvent are removed from the cast solution in a sequential manner by evaporation that is controlled by air flow over the film.

7. The method according to claim 1, in which the support is cooled such that a temperature difference of 10° C. exists between the support temperature and the upper critical solution temperature of the PMMA solution.

8. The method according to claim 1, in which the solution comprises 2-14 wt % PMMA and 55-96 wt % solvent/co-solvent.

9. The method according to claim 1, wherein the solvent is selected from the group consisting of dichloroethane, acetic acid, acetone, iso-propanol, n-propanol, n-butanol, chloroform, toluene, 1,4 dioxane, tetrahydrofuran, ethyl acetate, methyl ethyl ketone or a combination thereof.

10. The method according to claim 1, wherein the $C_2$-$C_6$ co-solvent is an alcohol selected from the group consisting of n-propanol, iso-propanol, 1-butanol, 2-butanol, tert-butanol, 2-methylbutan-2-ol, 3-methylbutan-2-ol, 2,2-dimethylpropan-1-ol, pentan-3-ol, pentan-2-ol, pentan-1-ol, 1-hexanol, 2-hexanol, 3-hexanol, 2-methyl-2-pentanol, 2,3-dimethyl-2-butanol, 3-methyl-3-pentanol and cyclohexanol.

11. The method according to claim 10, in which the PMMA membrane on the solid support material is rendered hydrophilic by treatment with any one of the following: hydrolysis, aminolysis, silanisation, aqueous solutions of surfactants, ultraviolet radiation, plasma treatment, electron beam radiation and ozonation, or combinations thereof while maintaining the ability to bind proteins via hydrophobic interactions.

12. A porous homogeneous and symmetric poly(methyl methacrylate) (PMMA) membrane on a solid support material produced by a method comprising the steps of:
    (i) mixing a suitable amount of PMMA, a solvent, and a $C_2$-$C_6$ co-solvent to produce a PMMA solution with increased sensitivity to temperature fluctuations, wherein the $C_2$-$C_6$ co-solvent functions as a solvent above a certain temperature and as a non-solvent below said certain temperature;
    (ii) casting a thin film of the PMMA solution onto a solid support material; and
    (iii) affecting the temperature of the cast PMMA solution on the solid support material so that the cast PMMA solution becomes unstable and separates out into two phases, and wherein the C2-C6 co-solvent transitions from a co-solvent in the solution to a non-solvent, thereby producing the homogenous and symmetric PMMA membrane on the solid support material.

13. The porous symmetric poly(methyl methacrylate) (PMMA) membrane on a solid support material according to claim 12 having a symmetric reticulated 3-D matrix structure and a porosity of at least 85%, as determined by weight volume calculations.

14. The porous symmetric poly(methyl methacrylate) (PMMA) membrane on a solid support material according to claim 12, wherein the membrane has an average pore size of 0.5-30 m.

15. A lateral flow diagnostic device comprising a reaction membrane, characterized in that the reaction membrane comprises a symmetric porous poly(methyl methacrylate) (PMMA) membrane and solid support composite according to claim 12.

16. A device for performing an immunoassay that comprises a homogenous and symmetric poly(methyl methacrylate) membrane on a solid support produced by a method comprising the steps of:
(i) mixing a suitable amount of PMMA, a solvent, and a $C_2$-$C_6$ co-solvent to produce a PMMA solution with increased sensitivity to temperature fluctuations, wherein the $C_2$-$C_6$ co-solvent functions as a solvent above a certain temperature and as a non-solvent below said certain temperature;
(ii) casting a thin film of the PMMA solution onto a solid support material; and
(iii) affecting the temperature of the cast PMMA solution on the solid support material so that the cast PMMA solution becomes unstable and separates out into two phases, and wherein the C2-C6 co-solvent transitions from a co-solvent in the solution to a non-solvent, thereby producing the homogenous and symmetric PMMA membrane on the solid support material.

* * * * *